US00PP17658P2

(12) United States Plant Patent
Zerr

(10) Patent No.: US PP17,658 P2
(45) Date of Patent: Apr. 24, 2007

(54) POINSETTIA PLANT NAMED 'FISMARS CREME'

(50) Latin Name: *Euphorbia pulcherrima*
Varietal Denomination: Fismars Creme

(75) Inventor: Katharina Zerr, Höhr-Grenzhausen (DE)

(73) Assignee: Florfis AG, Binningen (CH)

( * ) Notice: Subject to any disclaimer, the term of this patent is extended or adjusted under 35 U.S.C. 154(b) by 2 days.

(21) Appl. No.: 11/347,908

(22) Filed: Feb. 6, 2006

(51) Int. Cl.
*A01H 5/00* (2006.01)

(52) U.S. Cl. ..... Plt./304
(58) Field of Classification Search ..... Plt./304, Plt./302
See application file for complete search history.

(56) References Cited

U.S. PATENT DOCUMENTS

PP12,852 P2 * 8/2002 Jacobsen ..... Plt./304
PP14,977 P2 * 7/2004 Zerr ..... Plt./307

OTHER PUBLICATIONS

Broertjes et al., ("Application of Mutation Breeding Methods in the improvement of Vegetatively Propagated Crops," Elsevier Scientific Publishing Company, 1978, pp. 118–119).*

* cited by examiner

*Primary Examiner*—Anne Marie Grunberg
*Assistant Examiner*—S. B. McCormick-Ewoldt
(74) *Attorney, Agent, or Firm*—Jondle & Associates, P.C.

(57) ABSTRACT

A new Poinsettia plant particularly distinguished by medium size, overlapping, cream-white bracts with flat, rosette-like inflorescences, uniform deep green foliage, ovate leaves with nearly no lobes, a medium flowering response and a compact to medium size, round plant habit, is disclosed.

2 Drawing Sheets

Genus and species: *Euphorbia pulcherrima* (Willd. Ex Klotzsch).
Variety denomination: 'Fismars Creme'.

BACKGROUND OF THE NEW PLANT

The present invention comprises a new and distinct cultivar of poinsettia plant, botanically known as *Euphorbia pulcherrima* (Willd. Ex Klotzsch) and hereinafter referred to by the cultivar name 'Fismars Creme'. The new cultivar is the result of an induced mutation in the poinsettia plant 'Fismars' (U.S. Plant Pat. No. 14,977) made in the year 2003 in Ahrensburg, Germany.

In May 2003, young plants of 'Fismars' were irradiated in Ahrensburg, Germany. The treated plants were grown in Hillscheid, Germany, and were propagated by shoot tip cuttings. The resulting plants were screened for positive mutations and examined during the flowering period in Fall 2004. Among these plants, one plant was selected and asexually multiplied for further examination in 2004. As a result, it was concluded that this new poinsettia plant is distinguishable from any other poinsettia variety whose existence is known to the inventor.

The new cultivar was created in 2003 in Ahrensburg, Germany and has been asexually reproduced repeatedly by vegetative cuttings in Hillscheid, Germany over a two-year period. 'Fismars Creme' has not been observed under all possible environmental conditions. The present invention has been found to retain its distinctive characteristics through successive asexual propagations.

Plants Breeder's Rights for this cultivar were applied for in Europe on Feb. 9, 2005 and in Canada on Mar. 18, 2005.

SUMMARY OF THE INVENTION

The following are the most outstanding and distinguishing characteristics of this new cultivar when grown under normal horticultural practices in Hillscheid, Germany.

1. A cream-white bract color;
2. A medium size, flat, rosette-like inflorescence with an overlapping arrangement of bracts;
3. Uniform, deep green foliage with ovate leaves that have nearly no lobes;
4. A compact to medium size, round shaped plant habit; and
5. A medium flowering response.

DESCRIPTION OF PHOTOGRAPH

This new poinsettia plant is illustrated by the accompanying photographs which show overall plant habit including blooms, buds and foliage of the plant; the colors shown are as true as can be reasonably obtained by conventional photographic procedures. The photographs are of a whole plant about 18-weeks old and in full flower, grown in a greenhouse in Hillscheid, Germany, in early December of 2005.

DESCRIPTION OF THE NEW CULTIVAR

Figure 1:
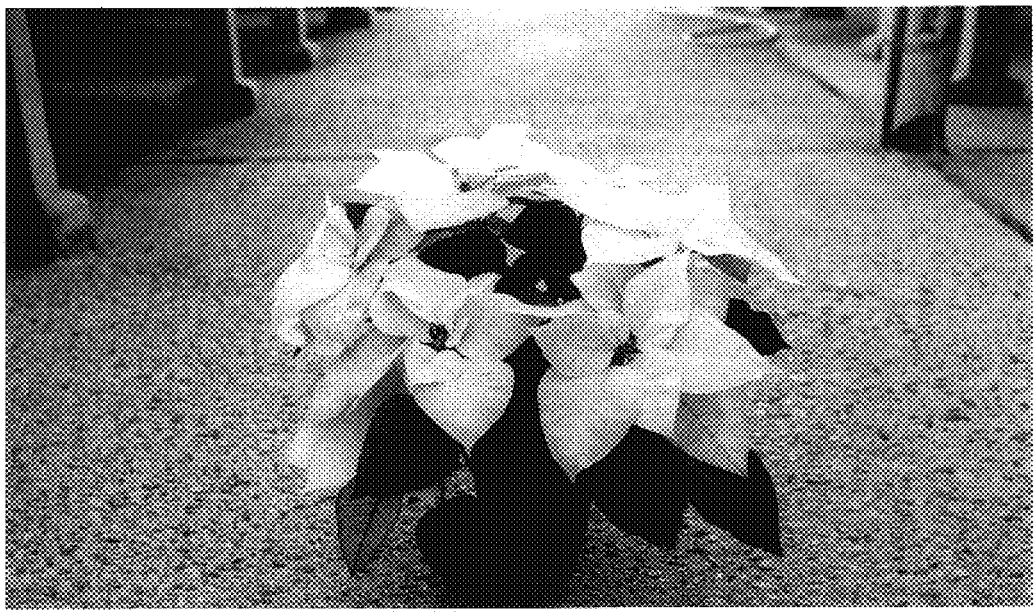
FIG. 1 shows the overall plant habit, including blooms, buds and foliage.
Figure 2:
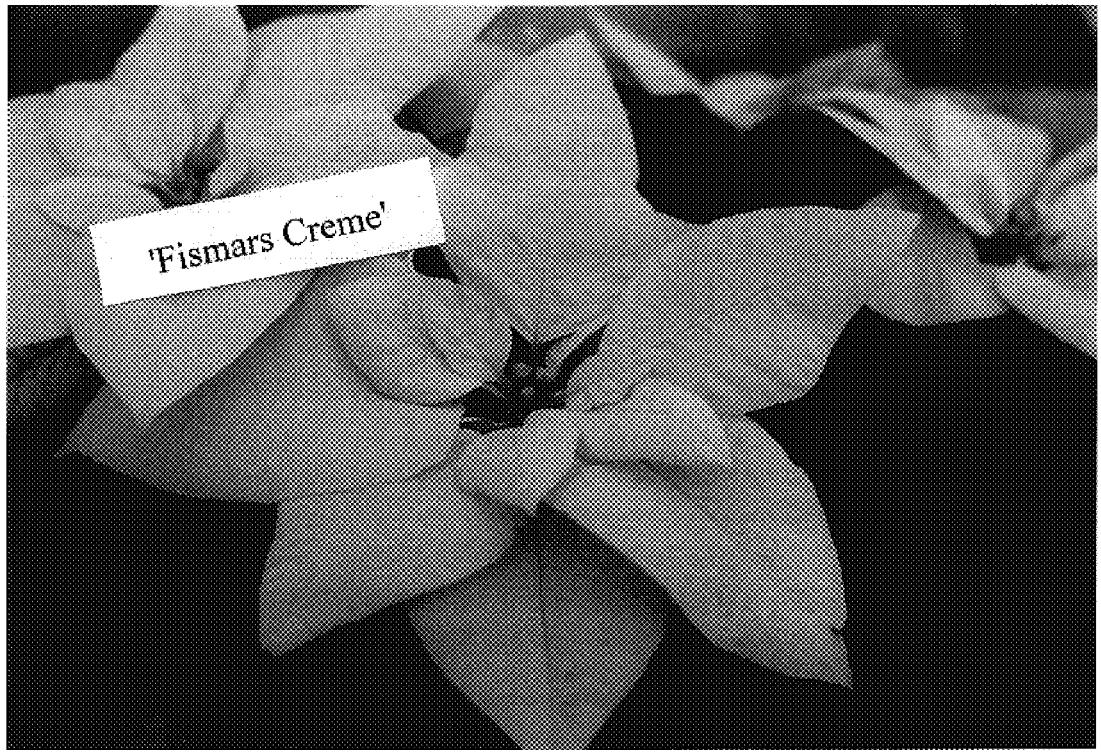
FIG. 2 shows a close-up of the mature inflorescences.

The following detailed description sets forth the distinctive characteristics of 'Fismars Creme'. The data which define these characteristics were collected from asexual reproductions carried out in Hillscheid, Germany. The plant history was taken on 18-week old plants which were planted as rooted cuttings in 14-cm pots on Jul. 28, 2005 and were pinched on Aug. 12, 2005, which left 7 to 8 leaves remaining. The plants were grown in a greenhouse at a minimum temperature of 18° C. and a ventilation temperature of 24° C. The plants initiated flowers under natural short-day conditions in the Fall. No black cloth was applied to the greenhouse to simulate short-day conditions. No growth regulator was applied. Color readings were taken under natural light in the greenhouse. Color references are primarily to The R.H.S. Colour Chart of The Royal Horticultural Society of London (R.H.S.) (2001).

DETAILED BOTANICAL DESCRIPTION OF THE NEW PLANT

Classification:
- *Family.*—Euphorbiaceae.
- *Botanical.*—*Euphorbia pulcherrima* (Willd. Ex Klotzsch).
- *Common name.*—Poinsettia.

Parentage: Mutation of the red-colored poinsettia plant 'Fismars' (U.S. Plant Pat. No. 14,977).

Growth:
- *Form.*—Shrub, self-branching.
- *Growth and branching habit.*—Compact to medium size; pinched plants are bushy and round in shape.
- *Height* (*from soil line to the top*).—23.5 cm.
- *Width.*—46 cm.
- *Time to produce a finished flowering plant.*—About 17 weeks (the total cultivation time) for a 14-cm pot or 9 weeks after the autumnal equinox (late November) when marketable quality is reached.
- *Time to initiate and develop roots.*—20 to 24 days in a greenhouse at 22° C. to 24° C.

Branches:
- *Average number.*—6.6.
- *Length of branches.*—20 cm to 23 cm.
- *Internode length.*—1.7 cm to 3.0 cm.
- *Diameter of branches.*—0.5 cm to 0.7 cm.
- *Stem color.*—Mainly RHS 143C (green) but is RHS 145A (light-green) near the tips.

Leaves:
- *Quantity.*—40 to 45 leaves per plant (6 to 7 leaves per branch).
- *Arrangement.*—Alternate.
- *Size.*—Length: 10.0 cm. Width: 7.8 cm.
- *Shape.*—Ovate.
- *Margin.*—Entire.
- *Apex.*—Acuminate.
- *Base.*—Truncate to round.
- *Lobes.*—Weak, rounded or pointed.
- *Color* (*mature leaves*).—Upper surface: Between RHS 137A and RHS 139A. Lower surface: RHS 137C.
- *Color* (*immature leaves*).—Upper surface: RHS 143A. Lower surface: RHS 137D.
- *Texture.*—Upper surface: Smooth and flat, only weakly veined. Lower surface: Flat and smooth, except for the slightly protruding midrib and finer side veins in a pinnate pattern.
- *Venation color.*—Upper surface: RHS 145A (light-green). Lower surface: RHS 145B (pale-green) to RHS 145C (pale-green).
- *Variegation.*—None.
- *Leaf petiole.*—Length: 5.7 cm. Diameter: 0.3 cm. Color: Upper surface: RHS 144B (yellowish-green). Lower surface: RHS 145B (pale-green). Texture: Glabrous. Aspect: Petioles are mostly horizontally directed, the leaf blades are slightly downward directed.

Bracts:
- *Number per inflorescence.*—10 to 13.
- *Shape.*—Ovate.
- *Apex.*—Acuminate.
- *Base.*—Rounded or obtuse.
- *Lobes.*—Almost no lobes.
- *Size.*—Length: 11 cm. Diameter: 9.0 cm to 9.5 cm.
- *Texture.*—Smooth to weakly rugose.
- *Bract color.*—Upper surface: RHS 4D (pale yellowish-white). Lower surface: RHS 11D.
- *Vein color.*—Upper surface: About RHS 4D (pale yellowish-white). Lower surface: RHS 145D (pale green) or lighter.
- *Bract petiole.*—Length: 1.0 cm to 2.0 cm. Diameter: 0.2 cm. Color: Upper surface: Near RHS 145C (light-green). Lower surface: RHS 4C (pale-yellow) to RHS 150C (yellowish-green).

Inflorescence:
- *Blooming habit.*—Beginning under natural short-day conditions in the Fall: Botanically (cyathia open): About early December Commercially (bracts colored, marketable): Late November.
- *Inflorescence type.*—Medium size, flat, mostly horizontally directed, the center a tight cyme with few cyathia.
- *Average number of inflorescences.*—6.4.
- *Lastingness.*—About 4 to 5 weeks with no dropping of bracts.
- *Diameter.*—21 cm to 23 cm.
- *Height.*—3.0 cm to 3.5 cm.

Cyme:
- *Cyme diameter.*—1.5 cm.
- *Cyathia number.*—5 in a tight cluster.
- *Cyathium.*—Shape: Ovate: Diameter: 0.5 cm to 0.6 cm. Length: 0.6 cm to 0.7 cm. Color: Mainly RHS 143C (light-green); near RHS 150D (pale yellowish-green) at top.
- *Peduncle.*—Color: RHS 143C (green). Length: 0.3 cm.
- *Nectar cups.*—Number: Most often two per cyathium. Size: 0.4 cm wide. Color: RHS 12A (yellow).

Reproductive organs:
- *Stamens.*—Number: Mostly none, but occasionally 1 to 5. Filaments: Color: RHS 150D to RHS 155A (white). Length: 0.3 cm. Pollen: None observed.
- *Pistils.*—No female flowers observed.

Fruit and seed set: No seed set observed so far.

Disease and Insect resistance: No particular resistance or susceptibility has been observed.

COMPARISON WITH PARENTAL AND COMMERCIAL CULTIVARS

'Fismars Creme' differs from the parental cultivar 'Fismars' (U.S. Plant Pat. No. 14,977) by having cream-white bracts and shorter leaves, while 'Fismars' has red bracts and longer leaves. Additionally, 'Fismars Creme' has an earlier flowering response and develops few to no stamens, while 'Fismars' has a normal number of stamens.

'Fismars Creme' differs from the commercial cultivar 'Fiscor Creme' (U.S. Plant Pat. No. 10,824), by having shorter bracts as well as leaves with few to no lobes, with branches that are more upright and a narrow plant habit compared to 'Fiscor Creme'. Additionally, 'Fismars Creme' develops few to no stamens while 'Fiscor Creme' develops about 20 stamens per cyathium.

I claim:

1. A new and distinct cultivar of Poinsettia plant as shown and described herein.

* * * * *